United States Patent
Liao et al.

(10) Patent No.: US 8,778,883 B2
(45) Date of Patent: Jul. 15, 2014

(54) FOAMY BIOMATERIAL FOR BIOLOGICAL TISSUE REPAIR

(75) Inventors: Chun-Jen Liao, Taipei (TW);
Sheng-Hong Tseng, Taipei (TW);
Huang-Chien Liang, Hsinchu (TW);
Yi-Chun Su, Taoyuan (TW); Pei-Chi Hsu, Xizhi (TW)

(73) Assignees: Industrial Technology Research Institute, Hsinchu (TW); National Taiwan University Hospital, Taipei (TW)

( * ) Notice: Subject to any disclaimer, the term of this patent is extended or adjusted under 35 U.S.C. 154(b) by 451 days.

(21) Appl. No.: 12/618,381

(22) Filed: Nov. 13, 2009

(65) Prior Publication Data

US 2011/0117199 A1   May 19, 2011

(51) Int. Cl.
*A61K 38/39* (2006.01)
*A61K 9/12* (2006.01)
*A61K 38/01* (2006.01)
*A61K 8/65* (2006.01)

(52) U.S. Cl.
CPC ............... *A61K 38/014* (2013.01); *A61K 9/12* (2013.01); *A61K 38/39* (2013.01); *A61K 8/65* (2013.01)
USPC ........................ 514/17.2; 424/45; 602/50

(58) Field of Classification Search
None
See application file for complete search history.

(56) References Cited

U.S. PATENT DOCUMENTS

| | | | |
|---|---|---|---|
| 2001/0013352 A1* | 8/2001 | Poisson et al. | 132/200 |
| 2003/0171773 A1* | 9/2003 | Carrison | 606/213 |
| 2005/0205086 A1* | 9/2005 | Tamarkin et al. | 128/200.23 |
| 2009/0175922 A1* | 7/2009 | Voytik-Harbin | 424/423 |

\* cited by examiner

*Primary Examiner* — H. Sarah Park
(74) *Attorney, Agent, or Firm* — Cesari and McKenna, LLP

(57) ABSTRACT

A kit for producing a foamed biocompatible material includes a container configured to sustain a high pressure, and a tissue-repair composition placed in the container. The composition contains a biocompatible material, a liquid carrier, and a gas. The container has an internal pressure of greater than 1 atm and less than 250 atm, and includes a valve and a nozzle for releasing from the nozzle a foam formed of the composition upon opening the valve. Methods of producing and applying the biocompatible material are also disclosed.

8 Claims, No Drawings

FOAMY BIOMATERIAL FOR BIOLOGICAL TISSUE REPAIR

FIELD OF THE INVENTION

The invention relates to foamy biomaterials for repairing biological tissues. The invention also relates to the methods of making and using the biomaterials.

BACKGROUND

Biocompatible materials, including natural and synthetic polymers, have been frequently used for tissue repair in various forms, e.g., bone cement, dural substitute, wound dressing, anti-postoperative adhesion membrane, and joint injection fluid. There is still a need for producing new biocompatible materials or new forms of biocompatible materials that are more convenient to use.

SUMMARY

In one aspect, the invention relates to a high-pressure kit for producing a foamed biocompatible material for tissue repair. The kit includes a container configured to sustain a high pressure and a tissue-repair composition placed in the container. The tissue-repair composition contains a biocompatible material, a liquid carrier, and a gas. The container has an internal pressure of greater than 1 atm and less than 250 atm, and includes a valve and a nozzle for releasing from the nozzle a foam formed of the composition upon opening the valve.

As used herein, a material is biocompatible if the material and any degradation products of the material are generally nontoxic to the recipient and also possess no significant deleterious or untoward effects on the recipient's body, such as a significant immunological reaction at the injection site. The term "tissue-repair composition" refers to a nontoxic composition suitable for repairing a wound. The term "nontoxic" refers to having sufficiently low toxicity to allow use in surgery and/or in therapeutics for the human or animal body. For example, the tissue-repair composition is free of typical components, such as detergents, and pigments, found in a topical cosmetic composition or consists essentially of natural polymers such as polypeptide. The term "a" or "an" refers to one or more. The term "foamed biocompatible material" or "foamy biocompatible material" refers to a wet foam or a bubbly liquid containing a biocompatible material.

Embodiments of the kit may include one or more of the following features. The kit can be free of a cross-linking agent. The container can have an internal pressure between 100 atm and 150 atm. The biocompatible material can be a polypeptide such as a protein (e.g., collagen), a polysaccharide (e.g., hyaluronic acid or its salts), or a combination thereof. The gas can be nontoxic gas such as air, oxygen, nitrogen, or carbon dioxide. Preferably, oxygen is used. The liquid carrier can be water.

In another aspect, the invention relates to a method for producing a foamed biocompatible material. The method includes providing a container, which includes a valve and a nozzle and is configured to sustain a high pressure, and opening the valve to release from the nozzle a foam formed of a tissue-repair composition contained in the container. The composition includes a biocompatible material, a liquid carrier, and a gas such that the container has an internal pressure of greater than 1 atm and less than 250 atm.

Embodiments of the method may include one or more of the following features. The biocompatible material can be a polypeptide, a polysaccharide, or a combination thereof. The biocompatible material is not cross-linked.

In still another aspect, the invention relates to a foamed biocompatible material, wherein the foamed biocompatible material has pores less than 250 µm in diameter and a pore density higher than 70%. The term "diameter" refers to the largest distance that can be formed between two opposite parallel lines tangent to pore boundary. The term "pore density" refers to the volume ratio of the pores or voids in the foamed biocompatible material.

In yet another aspect, the invention relates to a vacuum kit for producing a foamed biocompatible material for tissue repair as well as a method of producing a foamed biocompatible material by using the kit. The kit includes a container having a valve and an inlet and a tissue-repair composition containing a biocompatible material and a liquid carrier, in which the composition is placed in the inlet of the container, and the inside of container has a pressure lower than that of the outside so that upon opening the valve the composition is forced into the container by the pressure difference to form a foam inside the container. The method includes providing a container having a valve and an inlet, the inside of container having a pressure lower than that of the outside; placing in the inlet a tissue-repair composition containing a biocompatible material and a liquid carrier; and opening the valve so that the composition is forced into the container by the pressure difference to form a foam inside the container.

Also within the scope of the invention is a method for repairing a wound. The method includes providing the kit (either the high-pressure kit or the vacuum kit) of the invention described above and applying a foamed biocompatible material produced by the kit to the wound. In one embodiment, the applying step is performed by aiming the nozzle at a surface, opening the valve to release from the nozzle the foamed biocompatible material that adheres to the surface, detaching the foamed biocompatible material from the surface, and placing the foamed biocompatible material in or on the wound. In another embodiment, the applying step is performed by aiming the nozzle at the wound and opening the valve to release from the nozzle the foam biocompatible material that adheres to the wound, thereby repairing the wound. In yet another embodiment, the applying step is performed by opening the valve of the vacuum container to form a foamed biocompatible material inside the container, opening the container to obtain the foamed material, and placing the foamed material in or on the wound.

The details of one or more embodiments are set forth in the accompanying description below. Other aspects, features, and advantages will be apparent from the detailed description of embodiments and also from the appending claims.

DETAILED DESCRIPTION

This invention relates to a foamy form of biocompatible materials for surgical or therapeutic purposes. Preferably, the biocompatible material includes a polypeptide such as collagen. The foamy biocompatible materials of the invention are pliable and thus can completely fill a repair site of any shape or size. They are easy to make and apply to a wound by using the kit described herein. Their porous structure allows cells to grow and thus facilitate tissue regeneration. The foamy biocompatible materials of the invention are also hemostatic or capable of preventing postoperative adhesion.

As indicated above, the foamy biocompatible materials can be formed by operating the kit of the invention. The kit includes a container configured to sustain a high pressure and a tissue-repair composition placed in the container. The tissue-repair composition contains a biocompatible material, a liquid carrier, and a gas. The container includes a valve and a nozzle. In one embodiment, the container of the kit has an inner pressure grater than that of the surrounding atmosphere pressure. Thus, when the valve of the container is opened, the high-pressure gas in the container propels the biocompatible material and the liquid carrier out, thereby forming a wet foam at the nozzle of the container. The properties of the wet foam (such as pore size and pore density) can be selected by controlling the inner pressure, the speed of valve opening. For example, the pore size can be selected to be 10~250 μm by controlling open of the valve.

In another embodiment, the container of the kit has an inner pressure less than that of the surrounding atmosphere pressure; in other words, the tissue repair composition is kept in the container under vacuum. Thus, when the valve of the container is opened, the surrounding atmosphere gas gets into the container through the nozzle, thereby forming a wet foam inside the container. For example, a negative pressure is first obtained in the container by pumping air off the container; a funnel used as an inlet for the biomaterial is then connected to the nozzle of the container; upon adding 3% collagen to the funnel, the valve is opened to allow collagen solution be forced into the container to produce collagen foam; and the foam is taken out by opening the container.

In yet another embodiment, the biocompatible material and the liquid carrier are placed in a container under atmosphere pressure while the gas of a higher pressure was filled into a different container. When the two containers are connected, the high-pressure gas can get into the container having the biocompatible material to cause formation of wet foams.

The physical properties of the foam as formed (e.g., porosity, density, and adhesiveness) can be controlled by selecting the biocompatible material, the liquid carrier, concentration of the biocompatible material in the liquid carrier, pH value, and presence/absence of cross-linking agents. Suitable biocompatible materials include collagen, hyaluronic acid, gelatin, chitosan, alginate, and fibrinogen. Other examples are described in U.S. Pat. No. 6,730,299 and EP 747420. The tissue-repair composition may also contain biocompatible ceramic materials, such as calcium apatite, calcium sulfate, tricalcium phosphate beta, and hydroxyapatite. Examples of suitable liquid carriers include water, physiological saline, and phosphate buffered. When water or an aqueous solution is used as the liquid carrier, the pH value is preferably between 6 and 8. The concentration of the biocompatible material, preferably, ranges from 1% to 10%.

Without further elaboration, it is believed that the above description has adequately enabled the present invention. The following examples are, therefore, to be construed as merely illustrative, and not limitative of the remainder of the disclosure in any way whatsoever. All of the publications cited herein are hereby incorporated by reference in their entirety.

Example 1

Wet foams containing collagen were prepared according to the method of the invention and their properties tested.
(i) Preparing Collagen Solutions with Different Concentrations
1.5% collagen solution was prepared by mixing 1.5 g collagen and 100 ml of 0.1 N HCl at 4° C. and stirring the mixture until a homogeneous solution was formed. Solutions with 3% and 5% collagen were also prepared under the same conditions.

(ii) Neutralizing Collagen Solutions
A dialysis bag (MW 1100~14000) of an appropriate size was boiled in water for one minute. The bag was sealed at one end and moved to a sterilized operating table. The collagen solution was then disposed in the bag through the other end. Next, air was removed from the bag and the bag was sealed at the other end. The sealed bag was placed in 1×PBS until the collagen solution was neutralized. 100 ml of the collagen solution required about 10 liters of 1×PBS for dialysis.
(iii) Preparing Collagen Foam Spray Can
The neutralized collagen solution was first placed into a sterilized aluminum bottle having a pressure valve and nozzle. The valve of the bottle was opened to allow oxygen flowing in from a high-pressure oxygen cylinder until the internal pressure of the bottle reaches 110~420 atm. The valve of the bottle was then closed.
(iv) Preparing Collagen Wet Foam
The as-made spray can was held proximate to a surface. Then the pressure valve was opened. As a result, a wet gel was sprayed onto the surface.
(v) Properties of Wet Foam
Wet foams were produced from each of the three collagen solutions. Unexpectedly, all of the wet foams were stable with low fluidity and adhesive to the surface.

Example 2

Wet foams containing hyaluronic acid were prepared according to the method of the invention and their properties tested.

1% HA solution was prepared by mixing 1 g HA (MW 900,000) and 99 ml of double deionized water at 4° C. and stirring the mixture until a homogeneous solution was formed. Solution with 2% HA was also prepared under the same conditions.

Spray cans containing the HA solution and oxygen were prepared in the same manner as described in Example 1 above. Wet foams from the two HA solutions were obtained by opening the pressure valve of the spray can. It was observed that both wet foams were unstable and highly fluidic.

Example 3

Wet foams containing both collagen and hyaluronic acid were prepared according to the method of the invention and their properties tested.

At 4° C., the 3% neutralized collagen solution in Example 1 was mixed with an equal weight) of the 2% HA solution in Example 2. The resulting mixture was then homogenized in a homogenizer to obtain a homogeneous mixture solution.

A spray can containing the mixture solution and oxygen was prepared in the same manner as described in Example 1 above. A wet foam was obtained by opening the pressure valve of the spray can. It was observed that the foam was stable and adhesive to the surface on which it was spayed.

Example 4

Wet foams containing cross-linked and uncross-linked collagen were prepared according to the method of the invention and their properties tested.

1 ml of Epoxy (BDDE) cross-linking agent was added into 99 ml of 3% neutralized collagen solution. The mixture was stirred at 37° C. for 24 hours. The cross-linked collagen was filtered through a 100-mesh steel sieve. The residue was washed with clean water for 48 hours. 10 g of the cleaned residue was mixed with 100 ml of 3% neutralized collagen solution. The resulting mixture was then homogenized in a homogenizer to obtain a homogenous solution.

A spray can containing the homogeneous solution and oxygen was prepared in the same manner as described in Example 1 above. A wet foam was obtained by opening the pressure valve of the spray can. It was observed that the foam was stable, adhesive to the surface on which it was spayed, and had low fluidity.

Example 5

Wet foams containing cross-linked HA and uncross-linked collagen were prepared according to the method of the invention and their properties tested.

1 ml of Epoxy (BDDE) cross-linking agent was added into 99 ml of 2% HA solution. The mixture was stirred at 37° C. for 24 hours. The cross-linked HA was filtered through a 100-mesh steel sieve. The residue was washed with clean water for 48 hours. The cleaned residue was further filtered through a 200-mesh steel sieve. The as obtained residue was concentrated by a super filtration system to afford a 2% cross-linked HA solution. 10 g of the cross-linked HA solution was mixed with 100 ml of 3% neutralized collagen solution. The resulting mixture was then homogenized in a homogenizer to obtain a homogenous solution.

A spray can containing the homogeneous solution and oxygen was prepared in the same manner as described in Example 1 above. A wet foam was obtained by opening the pressure valve of the spray can. It was observed that the foam was stable, adhesive to the surface on which it was spayed, and had low fluidity.

Example 6

Wet foams containing uncross-linked collagen and ceramic powder were prepared according to the method of the invention and their properties tested.

6 g calcium hydroxyapatite powder was added into 94 ml of 3% neutralized collagen solution. The mixture was homogenized in a homogenizer at 4° C.

A spray can containing the homogenized mixture and oxygen was prepared in the same manner as described in Example 1 above. A wet foam was obtained by opening the pressure valve of the spray can. It was observed that the foam was stable, adhesive to the surface on which it was spayed, and had low fluidity.

Example 7

Application of collagen wet foam as dura substitutes was evaluated.

Three New Zealand white rabbits, each 2~2.5 Kg, underwent surgery to remove a certain portion of the skull and the dura underneath it. The spray can containing 3% neutralized collagen solution as prepared in Example 1 was used to spray collagen wet foam as dura substitutes onto the inner side of the piece of skull removed. The skull piece covered with the dura substitutes was then placed back into the skull void. Finally, the muscle and skin on the skull was sutured back together.

After the surgery, rabbits grow normally without inflammation. 3 months post operation, rabbits were sacrificed. Their skulls were retrieved and examined. It was observed that the skull piece placed back in had grown fixed with the surrounding bones. Tissue slices were normal indicating that there was no adverse effect.

Example 8

Wet foam containing collagen and ceramic powder was evaluated to work as a bone implant.

A hole of a 0.6-cm diameter was created in a hip bone of a New Zealand white rabbit (2~2.5 Kg) by drilling. The spray can containing 3% neutralized collagen solution and calcium hydroxyapatite as prepared in Example 6 was used to spray a wet foam as a bone implant to completely fill the hole. Finally, the muscle and skin on the skull was sutured back together.

After the surgery, rabbits grow normally without inflammation. 3 months post operation, the rabbit was sacrificed. Its hip bone was retrieved and examined. It was observed that new bone had grown in the hole. Tissue slices were normal indicating that there was no adverse effect.

Example 9

Collagen wet foam was evaluated to work as a wound dressing.

Three New Zealand white rabbits, each 2~2.5 Kg, underwent surgery to remove a 3 cm$^2$ area of skin. The spray can containing 3% neutralized collagen solution as prepared in Example 1 was used to spray collagen wet foam as a wound dressing onto the wound formed. A water-proof, air-permeable 3M film was placed on top of the treated area.

After the surgery, rabbits grow normally without inflammation. Tissue slices were normal indicating that there was no adverse effect.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A kit for producing a foamed biocompatible material for tissue repair, comprising:
   a container configured to sustain a high pressure of greater than 1 atm and less than 250 atm, and
   a tissue-repair composition placed in the container, the composition containing a neutralized and homogeneous solution at pH 6-8 that includes a biocompatible material, wherein the biocompatible material consists of collagen at a concentration of 1%-10%, a liquid carrier that is water, physiological saline, or phosphate buffered saline, and a gas that is air, oxygen, nitrogen, or carbon dioxide,
   wherein the container has an internal pressure of greater than 1 atm and less than 250 atm, and includes a valve and a nozzle for releasing from the nozzle a foam formed of the composition upon opening the valve, and wherein the kit is free of a cross-linking agent.

2. The kit of claim 1, wherein the container has an internal pressure between 100 atm and 150 atm.

3. A method for producing a foamed biocompatible material, the method comprising:
   providing a container configured to sustain a high pressure such that the container has an internal pressure of greater than 1 atm and less than 250 atm, wherein the container includes a valve, a nozzle, and a tissue-repair composition containing a neutralized and homogeneous solution at pH 6-8 that includes a biocompatible material, wherein the biocompatible material consists of collagen at a concentration of 1%-10%, a liquid carrier that is water, physiological saline, or phosphate buffered saline, and a gas that is air, oxygen, nitrogen, or carbon dioxide; and
   opening the valve to release from the nozzle a foam formed of the tissue-repair composition.

4. The kit of claim 1, wherein the concentration of collagen is 1.5%-5%.

5. The method of claim 3, wherein the container has an internal pressure between 100 atm and 150 atm.

6. A method for repairing a wound, the method comprising: providing the kit of claim 4, and applying a foamed biocompatible material produced by the kit to the wound.

7. The method of claim 6, wherein the applying step is performed by aiming the nozzle at a surface, opening the valve to release from the nozzle the foamed biocompatible material that adheres to the surface, detaching the foamed biocompatible material from the surface, and placing the foamed biocompatible material in or on the wound.

8. The method of claim 6, wherein the applying step is performed by aiming the nozzle at the wound and opening the valve to release from the nozzle the foam biocompatible material that adheres to the wound, thereby repairing the wound.

* * * * *